US012807597B2

(12) United States Patent
Ueda et al.

(10) Patent No.: US 12,807,597 B2
(45) Date of Patent: Nov. 24, 2026

(54) METHOD FOR PRODUCING 1,3-BENZODIOXOLE DERIVATIVE

(71) Applicant: DAIICHI SANKYO COMPANY, LIMITED, Tokyo (JP)

(72) Inventors: Tsuyoshi Ueda, Tokyo (JP); Yuji Kaiya, Tokyo (JP); Takahisa Uchida, Tokyo (JP); Makoto Imai, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 1008 days.

(21) Appl. No.: 18/012,090

(22) PCT Filed: Jul. 7, 2021

(86) PCT No.: PCT/JP2021/025537

§ 371 (c)(1),
(2) Date: Dec. 21, 2022

(87) PCT Pub. No.: WO2022/009911

PCT Pub. Date: Jan. 13, 2022

(65) Prior Publication Data

US 2023/0257368 A1 Aug. 17, 2023

(30) Foreign Application Priority Data

Jul. 8, 2020 (JP) ................................ 2020-117639

(51) Int. Cl.
*C07D 405/12* (2006.01)
*C07C 67/307* (2006.01)
*C07D 263/56* (2006.01)

(52) U.S. Cl.
CPC .......... *C07D 405/12* (2013.01); *C07C 67/307* (2013.01); *C07D 263/56* (2013.01)

(58) Field of Classification Search
CPC .................................................... C07D 405/12
See application file for complete search history.

(56) References Cited

U.S. PATENT DOCUMENTS

| | | | |
|---|---|---|---|
| 10,434,091 | B2 | 10/2019 | Watanabe et al. |
| 2006/0089495 | A1 | 4/2006 | Blagg et al. |
| 2010/0197908 | A1 | 8/2010 | Lehmann-Lintz et al. |

FOREIGN PATENT DOCUMENTS

| | | | |
|---|---|---|---|
| CN | 106883125 | A | 6/2017 |
| JP | 2007-161674 | A | 6/2007 |
| JP | 2010-512366 | A | 4/2010 |
| JP | 2020-045306 | A | 3/2020 |
| WO | WO-2015/141616 | A1 | 9/2015 |
| WO | WO-2019/204490 | A1 | 10/2019 |

OTHER PUBLICATIONS

European Extended Search Report issued in corresponding European Patent Application No. 21836791.0 dated Jul. 8, 2024 (8 pages).
Watson, William David, "Regioselective para-chlorination of activated aromatic compounds," The Journal of Organic Chemistry, vol. 50, Issue 12, 1985, pp. 2145-2148.
Lengyel et al., "t-Butyl Hypochlorite: A Powerful Electrophilic Aromatic Ring Chlorinating Agent," Synthetic Communications, An International Journal for Rapid Communication of Synthetic Organic Chemistry, vol. 28, Issue 10, 1998, pp. 1891-1896.
International Searching Authority, "International Search Report," issued in connection with International Patent Application No. PCT/JP2021/025537, dated Sep. 7, 2021.
International Searching Authority, "Written Opinion," issued in connection with International Patent Application No. PCT/JP2021/025537, dated Sep. 7, 2021.

*Primary Examiner* — Golam M Shameem
(74) *Attorney, Agent, or Firm* — Foley & Lardner LLP

(57) ABSTRACT

An object of the present invention is to provide an industrially useful and novel process for producing a 1,3-benzodioxole derivative, with high yield and few impurities, including a novel chlorination reaction of a benzene ring. In the novel process for producing a 1,3-benzodioxole derivative, it has been found that an industrially useful and novel chlorination reaction of a benzene ring is conducted by using sulfuryl chloride with high yield and few impurities. Based on the finding, the invention has been accomplished.

14 Claims, 1 Drawing Sheet

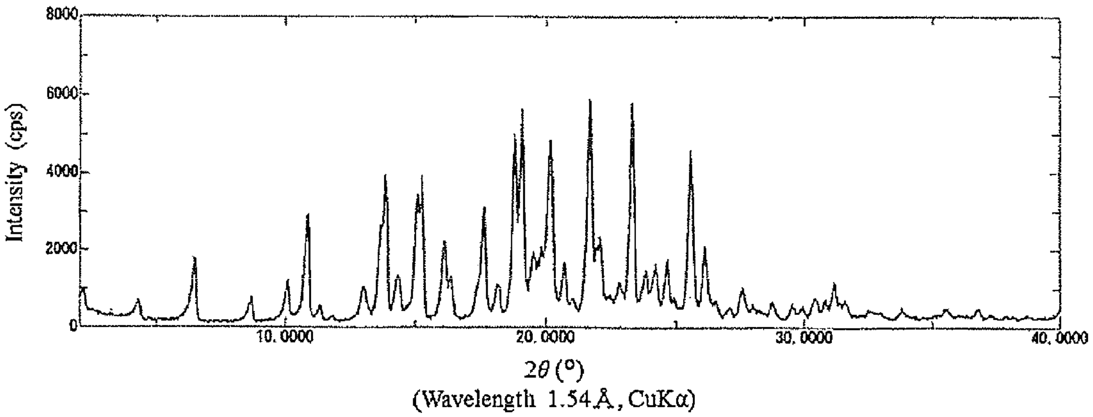
8000
6000
4000
2000
0
Intensity (cps)
10.0000
20.0000
30.0000
40.0000
2θ (°)
(Wavelength 1.54Å, CuKα)

METHOD FOR PRODUCING 1,3-BENZODIOXOLE DERIVATIVE

CROSS-REFERENCE TO RELATED APPLICATIONS

The present application claims priority under 37 U.S.C. § 371 to International Patent Application No. PCT/JP2021/025537, filed Jul. 7, 2021, which claims priority to and the benefit of Japanese Patent Application No. 2020-117639, filed on Jul. 8, 2020. The contents of these applications are hereby incorporated by reference in their entireties.

TECHNICAL FIELD

The present invention relates to a novel process for producing a 1,3-benzodioxole derivative, and particularly to a production process including a novel chlorination reaction of a benzene ring.

BACKGROUND ART

It is known that 1,3-benzodioxole derivatives are useful as medicines or raw materials for producing medicines and useful for treating tumors (Patent Literature 1).

Patent Literature 1 discloses various 1,3-benzodioxole derivatives and processes for producing them. The production processes disclosed in the literature have a characteristic feature that a chlorine atom is introduced into a benzene ring by using N-chlorosuccinimide (Patent Literature 1, Reference Example 2). Besides this, processes for introducing a chlorine atom into a benzene ring using chlorine gas (Non Patent Literature 1) and reagents such as t-BuOCl, are known (Non Patent Literature 2). However, until now, a chlorination reaction using sulfuryl chloride to introduce a chlorine atom with high yield and few impurities has not been known.

CITATION LIST

Patent Literature

Patent Literature 1: WO2015141616

Non Patent Literature

Non Patent Literature 1: Watson, W. D. J. Org. Chem. 1985, 50, 2145.

Non Patent Literature 2: Lengyel, I.; Cesare, V.; Stephani, R. Synth. Commun. 1998, 28, 1891.

SUMMARY OF INVENTION

Technical Problem

An object of the present invention is to provide an industrially useful and novel process for producing a 1,3-benzodioxole derivative, with high yield and few impurities, including a novel chlorination reaction of a benzene ring.

Solution to Problem

The present invention relates to the following (1) to (10).

(1) A production method comprising chlorinating a compound represented by formula (I):

[Formula 1]

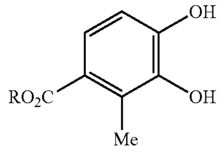

(I)

with sulfuryl chloride in a solvent to obtain a compound represented by formula (II):

[Formula 2]

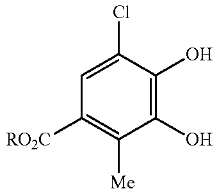

(II)

wherein in formula (I) and formula (II), R represents a $C_1$-$C_6$ alkyl group.

(2) The production method according to (1), wherein the solvent is a solvent comprising at least one selected from toluene, acetonitrile, methyl tert-butyl ether and cyclopentyl methyl ether, and water.

(3) The production method according to (1) or (2), wherein the solvent is a solvent comprising toluene, acetonitrile and water.

(4) The production method according to (1), wherein the solvent is at least one solvent selected from acetonitrile, ethyl acetate, tetrahydrofuran, dimethylacetamide and cyclopentyl methyl ether.

(5) The production method according to any one of (1) to (4), further comprising reacting the compound represented by formula (II) with tert-butyl (trans-4-ethynylcyclohexyl) carbamate using a ruthenium catalyst to obtain a compound represented by formula (III):

[Formula 3]

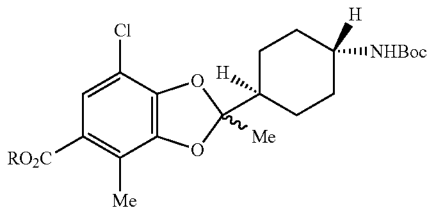

(III)

wherein in formula (III), R is the same as defined in (1).

(6) The production method according to (5), wherein the ruthenium catalyst is a catalyst comprising $Ru_3(CO)_{12}$ and $P(o\text{-}Tol)_3$.

(7) The production method according to any one of (1) to (6), wherein R is a methyl group.

(8) The production method according to any one of claims 5 to 7, further comprising subjecting the compound represented by formula (III) to (i) a step of performing hydrolysis, (ii) a step of performing optical resolution using an optically active amine, (iii) a step of removing a Boc group, and (iv) a step of performing dimethylation of a nitrogen atom to obtain a compound represented by formula (IV):

[Formula 4]

(IV)

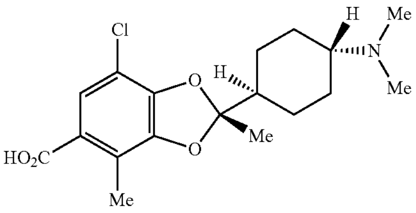

or a pharmaceutically acceptable salt thereof.

(9) The production method according to (8), wherein the optically active amine is (1S)-1-phenylethanamine.

(10) The production method according to (8) or (9), further comprising condensing the compound represented by formula (IV) with 3-(aminomethyl)-4,6-dimethylpyridin-2(1H)-one or a salt thereof to obtain a compound represented by formula (V):

[Formula 5]

(V)

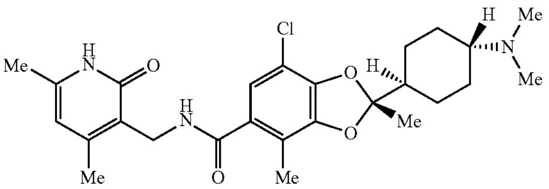

or a pharmaceutically acceptable salt thereof.

Advantageous Effects of Invention

In a novel process for producing a 1,3-benzodioxole derivative, it has been found that an industrially useful and novel chlorination reaction of a benzene ring can be conducted with high yield and few impurities by using sulfuryl chloride. Based on the finding, the present invention has been accomplished.

BRIEF DESCRIPTION OF DRAWING

The FIGURE shows a powder X-ray diffraction pattern of the crystals of the compound produced in Example 7. The vertical axis of the FIGURE represents diffraction intensity as relative X-ray intensity and the horizontal axis represents a value of diffraction angle, 2θ.

DESCRIPTION OF EMBODIMENTS

In the present invention, the "$C_1$-$C_6$ alkyl group" is a linear or branched alkyl group having 1 to 6 carbon atoms. Examples thereof include a methyl group, an ethyl group, a propyl group, an isopropyl group, a butyl group, an isobutyl group, a s-butyl group, a t-butyl group, a pentyl group, an isopentyl group, a 2-methylbutyl group, a neopentyl group, a 1-ethylpropyl group, a hexyl group, an isohexyl group and a 4-methylpentyl group.

In the present invention, the "ruthenium catalyst" means a catalyst formed of a ruthenium atom-containing compound and a ligand. Examples of the ruthenium atom-containing compound include $Ru_3(CO)_{12}$, $[RuCl_2(CO)_3]_2$, $Ru(acac)_3$, $[RuCl_2(benzene)]$, $[RuCl_2(mes)]_2$, $[RuCl_2(p\text{-}cym)]_2$ and $RuCl_2$ (1,5-cyclooctadiene). Preferably, $Ru_3(CO)_{12}$ is used. Examples of the ligand include $P(o\text{-}Tol)_3$, $P(tBu)_3$ (HBF) and $P(2\text{-}MeOPh)_3$. Preferably, $P(o\text{-}Tol)_3$ is used.

A preferable combination of a ruthenium atom-containing compound and a ligand is a combination of $Ru_3(CO)_{12}$ and $P(o\text{-}Tol)_3$.

In the present invention, a reaction can be carried out using an extremely small amount of a ruthenium catalyst. The equivalent amount of ruthenium catalyst to be used relative to the compound represented by formula (II) is 0.1 to 10 mol %, preferably 0.5 to 5 mol %, and more preferably 1 mol %. The equivalent amount of ruthenium atom relative to the compound represented by formula (II) is 0.3 to 30 mol %, preferably 1.5 to 15 mol %, and more preferably 3 mol %.

The "optically active amine" that can be used in the present invention is not limited as long as it can form a diastereomeric salt with a racemic compound having an acidic group and optical resolution can be carried out based on difference in solubility of the diastereomeric salt in a solvent. Examples of the optically active amine include (1S)-1-phenylethanamine and (2S)-2-amino-3-phenyl-1-propanol. Preferably, (1S)-1-phenylethanamine is used.

In the present invention, a "step of removing a Boc group" and a "step of performing dimethylation of a nitrogen atom" include not only a two-step reaction of removing a Boc group to isolate an intermediate and then performing dimethylation of a nitrogen atom, but also a one-pot reaction of removing a Boc group simultaneously with dimethylation of a nitrogen atom.

Examples of a reagent that can be used for removing a Boc group include hydrochloric acid, p-toluenesulfonic acid, formic acid and trifluoroacetic acid. Preferably, hydrochloric acid is used. Examples of the reagent that can be used for performing dimethylation of a nitrogen atom include formaldehyde and formic acid, formaldehyde and sodium triacetoxyborohydride. Preferably, formaldehyde and formic acid are used.

The solvent that can be used in the present invention is not limited as long as it is inert to each reaction. In the chlorination reaction using sulfuryl chloride, not only a single organic solvent but also a mixture of an organic solvent and water, can be used. When the organic solvent is used alone, at least one solvent selected from acetonitrile, ethyl acetate, tetrahydrofuran, dimethylacetamide (DMAc) and cyclopentyl methyl ether (CPME), and the like can be used. Preferably, at least one solvent selected from acetonitrile, ethyl acetate, tetrahydrofuran and cyclopentyl methyl ether (CPME) is used. When a mixture of an organic solvent and water is used, for example, a mixture of at least one solvent selected from toluene, acetonitrile, methyl tert-butyl ether (MTBE) and cyclopentyl methyl ether, and water, can be used. Preferably, a mixture of toluene, acetonitrile and water is used. In a reaction with tert-butyl (trans-4-ethynylcyclohexyl)carbamate using a ruthenium catalyst, for example, toluene, α,α,α-trifluorotoluene, chlorobenzene, butyl acetate, and/or methyl isobutyl ketone can be used. Preferably, toluene is used.

In the present invention, in a compound represented by formula (I), a compound represented by formula (II), a compound represented by formula (III), a compound represented by formula (IV) or a salt thereof and a compound represented by formula (V) or a salt thereof, all isomers (diastereoisomers, optical isomers, geometric isomers, rotational isomers) thereof are included.

In the present invention, the "pharmaceutical acceptable salt" refers to a salt having no significant toxicity and able to be used for a pharmaceutical composition. In the present invention, each of a compound represented by formula (IV) and a compound represented by formula (V) can form a salt by reacting it with an acid. Examples of the salt include salts of a hydrohalic acid such as a salt of hydrofluoric acid, a hydrochloride, a hydrobromide and a hydroiodide; inorganic salts such as a nitrate, a perchlorate, a sulfate and a phosphate; $C_1$-$C_6$ alkylsulfonates such as methanesulfonate, trifluoromethanesulfonate and ethanesulfonate; arylsulfonates such as benzenesulfonate and p-toluenesulfonate; organic salts such as an acetate, a malate, a fumarate, a succinate, a citrate, a ascorbate, a tartrate, an oxalate and an adipate; and amino acid salts such as a glycine salt, a lysine salt, an arginine salt, an ornithine salt, a glutamic acid salt and an aspartate.

In the present invention, a compound represented by formula (I), a compound represented by formula (II), a compound represented by formula (III), a compound represented by formula (IV) or a salt thereof and a compound represented by formula (V) or a salt thereof, when they are left in the air or recrystallized, sometimes absorb water molecule(s) to form hydrates. These hydrates are also included in the present invention.

In the present invention, a compound represented by formula (I), a compound represented by formula (II), a compound represented by formula (III), a compound represented by formula (IV) or a salt thereof and a compound represented by formula (V) or a salt thereof, when they are left in a solvent or recrystallized, sometimes absorb certain solvents to form solvates. These solvates are also included in the present invention.

Next, the present invention will be described. The reaction conditions of the present invention should not be construed as being limited to those described below. In the present invention, a functional group of a compound is sometimes protected with an appropriate protecting group. Examples of such functional groups include a hydroxy group, a carboxy group and an amino group. With respect to the types of protecting groups and conditions for introducing or removing the protecting groups, refer to, e.g., Protective Groups in Organic Synthesis (T. W. Green and P. G. M. Wuts, John Wiley & Sons, Inc., New York, 2006).

EXAMPLES

The present invention will be described in more detail by way of Examples but the scope of the present invention is not limited by these Examples. The abbreviations used in Examples and their meanings are as follows:

mg: milligram, g: gram, kg: kilogram, mL: milliliter, L: liter, MHz: megahertz, rt: room temperature, ND: not detected.

In the following Examples, nuclear magnetic resonance (hereinafter referred to as $^1H$ NMR: 500 MHz) spectra were obtained by using tetramethylsilane as a reference substance, and chemical shift values were expressed by δ values (ppm). As a split pattern, a singlet was indicated by s, a doublet by d, a triplet by t, a quartet by q, a multiplet by m, and a broad (line) by br. In the Examples of the present invention, HPLC 10A (SHIMADZU) or ACQUITY UPLC H-Class (WATERS) was used as "liquid chromatography".

In the Examples, the instrument used for X-ray powder diffraction analysis and analytical conditions are as follows.

Model: Rigaku Rint TTR-III
Sample: appropriate amount
X-ray generation conditions: 50 kV, 300 mA
Wavelength: 1.54 angstroms (Co-Kα ray)
Measurement temperature: room temperature
Scanning speed: 20°/min
Scanning range: 2 to 40°
Sampling width: 0.02°

(Reference Example 1) Production of ethyl trans-4-[(tert-butoxycarbonyl)amino]cyclohexanecarboxylate

[Formula 6]

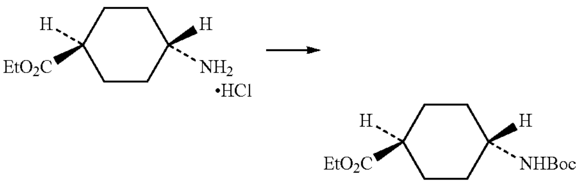

To a reaction vessel, ethanol (624 L) and ethyl trans-4-aminocyclohexanecarboxylate monohydrochloride (138.7 kg, 667.8 mol) were added, under a nitrogen atmosphere. The reaction solution was cooled, and then triethylamine (151.2 kg, 1495.5 mol) and di-tert-butyl dicarbonate (160.9 kg, 737.2 mol) were each added dropwise while keeping them at 20° C. or less. After the reaction mixture was stirred at 20-25° C. for 4 hours, water (1526 kg) was added dropwise to the mixture at 25° C. or less and the mixture was further stirred for 2 hours. The solid substance precipitated was obtained by filtration, washed with a mixture of ethanol: water=1:4 (500 L) and dried under reduced pressure at 40° C. to obtain the title compound (169.2 kg (yield 93.4%)). $^1H$ NMR (500 MHz, $CDCl_3$): δ 4.37 (br, 1H), 4.11 (q, J=2.8 Hz, 2H), 3.41 (br, 1H), 2.20 (tt, J=4.8, 1.4 Hz, 1H), 2.07 (m, 2H), 2.00 (m, 2H), 1.52 (dq, J=4.6, 1.4 Hz, 2H), 1.44 (s, 9H), 1.24 (t, J=2.8 Hz, 3H), 1.11 (dq, J=4.6, 1.4 Hz, 2H)

(Reference Example 2) Production of tert-butyl [trans-4-(hydroxymethyl)cyclohexyl]carbamate

[Formula 7]

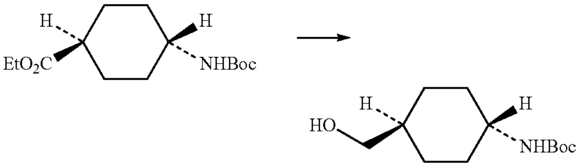

To a reaction vessel, tetrahydrofuran (968 kg), ethyl trans-4-[(tert-butoxycarbonyl)amino]cyclohexanecarboxylate (110 kg, 405.4 mol), lithium chloride (27.5 kg, 648.6 mol), potassium borohydride (32.8 kg, 608.1 mol) and water (2.9 L, 162.2 mol) were added, under a nitrogen atmosphere.

The reaction solution was slowly warmed up to 50° C., stirred further for 6 hours and cooled to 0-5° C. Acetone (66 L) and a 9 wt % aqueous ammonium chloride solution (1210 kg) were each added dropwise to the reaction solution while keeping them at 20° C. or less. The solution was stirred at 20-25° C. for one hour. To the solution, ethyl acetate (550 L) was further added. After the water layer was discarded, the organic layer was concentrated to 550 L. To the residue, ethyl acetate (1650 L) and a 9 wt % aqueous ammonium chloride solution (605 kg) were added. After stirring the mixture, the water layer was discarded and the organic layer was further washed sequentially with a 9 wt % aqueous ammonium chloride solution (605 kg), a 9% aqueous sodium chloride solution (605 kg) and water (550 L). The organic layer was concentrated to 880 L. To the residue, ethyl acetate (660 L) was added. The mixture was concentrated up 880 L while keeping the internal temperature thereof at 40-50° C. After the residue was cooled to 0-5° C. and further stirred for one hour, petroleum ether (1760 L) was added dropwise to the residue over 30 minutes. The mixture was stirred at the same temperature for 2 hours. The solid substance precipitated was obtained by filtration, washed with a mixture of petroleum ether:ethyl acetate=3:1 (220 L) cooled to 0-5° C., and dried under reduced pressure at 40° C. to obtain the title compound (86.0 kg (yield 92.3%)). $^1$HNMR (500 MHz, $CDCl_3$): δ 4.37 (br, 1H), 3.45 (d, J=2.2 Hz, 2H), 3.38 (br, 1H), 2.04 (m, 2H), 1.84 (m, 2H), 1.44 (m, 10H), 1.28-1.31 (m, 1H), 1.00-1.13 (m, 4H)

(Reference Example 3) Production of tert-butyl [trans-4-(2,2-dibromoethenyl)cyclohexyl]carbamate

[Formula 8]

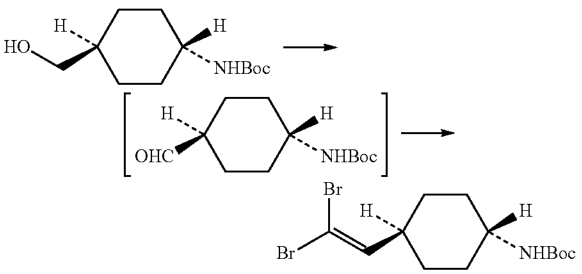

(Step 1)

To a reaction vessel, ethyl acetate (50 L), tert-butyl [trans-4-(hydroxymethyl)cyclohexyl]carbamate (2.5 kg, 10.90 mol), potassium bromide (39.3 g, 0.33 mol), 2,2,6,6-tetramethylpiperidin-1-oxyl (51.1 g, 0.33 mol) and a 4.8% sodium hydrogen carbonate solution (26.25 kg) were added, under a nitrogen atmosphere. The reaction solution was cooled to 0-5° C. and 9.9% sodium hypochlorite (8.62 kg, 11.45 mol) was added to the reaction solution at 5° C. or less. The resultant reaction solution was further stirred at 0° C. for 4 hours. To the mixture, sodium sulfite (250 g) was added. After being stirred at 0-5° C. for 30 minutes, the solution was warmed to 20-25° C. Thereafter, the water layer was discarded, the organic layer was washed with a 20% aqueous sodium chloride solution (12.5 kg), dried over sodium sulfate and concentrated to 7.5 L. To the residue, ethyl acetate (12.5 L) was added and the mixture was again concentrated to 7.5 L to obtain a tert-butyl (trans-4-formylcyclohexyl)carbamate solution, which was subjected to the subsequent reaction.

(Step 2)

To a reaction vessel, tetrahydrofuran (30 L) and triphenylphosphine (5.72 kg, 21.8 mol) were added, under a nitrogen atmosphere. The reaction solution was warmed to 40° C. and stirred for 5 minutes. To the reaction solution, carbon tetrabromide (3.61 kg, 10.9 mol) was added over 30 minutes. The reaction mixture was further stirred at 40-45° C. for 30 minutes. To the reaction mixture, a mixture of a tert-butyl (trans-4-formylcyclohexyl) carbamate solution and triethylamine (2.54 kg, 25.1 mol) was added at less than 45° C. over 20 minutes. The resultant reaction mixture was further stirred at 40° C. for 15 hours and cooled to 0° C. Thereafter, water (0.2 L) was added to the mixture at 10° C. or less and further water (25 L) was added. After the reaction solution was warmed to 20-25° C., the water layer was discarded. To the organic layer, ethyl acetate (4.5 kg) and a 10% aqueous sodium chloride solution (25 kg) were added. After stirring, the water layer was again discarded. The organic layer obtained was concentrated to 15 L, and 2-propanol (19.65 kg) was added thereto. The mixture was concentrated to 17.5 L. To the residue, 2-propanol (11.78 kg) and 5 mol/L hydrochloric acid (151.6 g) were added. The mixture was stirred at 25-35° C. for 2.5 hours. To the mixture obtained, water (16.8 L) was added dropwise. The mixture was stirred at 20-25° C. for 30 minutes, and then at 0° C. for 2 hours. The solid substance precipitated was obtained by filtration, washed with a mixture of acetonitrile: water=60:40 (11 kg) cooled to 0-5° C., and dried under reduced pressure at 40° C. to obtain the title compound (3.05 kg (yield 73.0%)). $^1$HNMR (500 MHz, $CDCl_3$): δ 6.20 (d, J=3.6 Hz, 1H), 4.37 (br, 1H), 3.38 (br, 1H), 2.21 (dtt, J=3.6, 4.6, 1.4 Hz, 1H), 2.05-2.00 (m, 2H), 1.80-1.83 (m, 2H), 1.44 (s, 9H), 1.23 (ddd, J=9.9, 5.3, 1.2 Hz, 2H), 1.13 (ddt, J=4.6, 1.4, 5.2 Hz, 2H)

(Reference Example 4) Production of tert-butyl (trans-4-ethynylcyclohexyl)carbamate

[Formula 9]

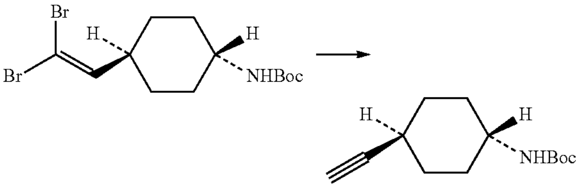

To a reaction vessel, toluene (1436 kg), tert-butyl [trans-4-(2,2-dibromoethenyl)cyclohexyl]carbamate (110 kg, 287.1 mol) and N,N,N',N'-tetramethylethane-1,2-diamine (106.7 kg, 918.8 mol) were added, under a nitrogen atmosphere. The reaction solution was cooled to −10° C. To the reaction solution, an isopropylmagnesium chloride-tetrahydrofuran solution (2.0 mol/L, 418 kg, 863 mol) was added dropwise at −5° C. or less. The reaction solution was stirred at −10° C. for 30 minutes. After completion of the reaction, 5 mol/L hydrochloric acid (465 kg) was added at 5° C. or less to the reaction solution. The reaction solution was warmed to 20-25° C. and the pH of the solution was adjusted to 5.0-6.0 with 5 mol/L hydrochloric acid (41.8 kg). After the water layer was discarded, the organic layer was washed twice with water (550 L) and concentrated to 550 L. To the concentrate, 2-propanol (1296 kg) was added. The mixture was concentrated again to 550 L. To the residue, 2-propanol (1296 kg) was further added. The mixture was concentrated to 550 L, and then water (770 L) was divided into 4 portions, which were separately added dropwise to the mixture. Every time water was added, the mixture was stirred for 30 minutes. After completion of addition, the mixture was stirred for one hour, and further at 0° C. for one hour. The solid substance precipitated was obtained by filtration, washed with a mixture of 2-propanol:water=5:7 (550 L) cooled to 0-5° C. and dried under reduced pressure at 40° C. to obtain the title compound (57.8 kg (yield 90.2%)).

$^1$HNMR (500 MHz, $CDCl_3$): δ 4.36 (br, 1H), 3.43 (br, 1H), 2.18-2.23 (m, 1H), 1.97-2.04 (m, 5H), 1.44-1.56 (m, 11H), 1.06-1.14 (m, 2H)

(Reference Example 5) Production of 4,6-dimethyl-2-oxo-1,2-dihydropyridine-3-carbonitrile

[Formula 10]

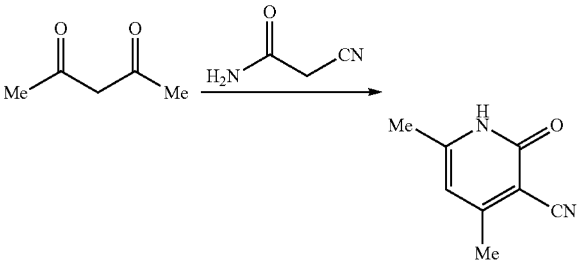

To a reaction vessel, water (300 L), 2-cyanoacetamide (20 kg, 238 mol), 1-pentane-2-4-dione (26.2 kg, 262 mol) and potassium carbonate (3.29 kg, 23.8 mol) were added, under a nitrogen atmosphere. The reaction mixture was stirred at room temperature for 6 hours or more. After completion of the reaction, the solid substance precipitated was obtained by filtration, washed with water (60 L), followed with a mixture of methanol (40 L) and water (40 L), and dried under reduced pressure at 40° C. to obtain the title compound (34.3 kg (yield 97.3%)).

$^1$H NMR (500 MHz, DMSO-$d_6$): δ 2.22 (s, 3H), 2.30 (s, 3H), 6.16 (s, 1H), 12.3 (brs, 1H)

(Reference Example 6) Production of 3-(aminomethyl)-4,6-dimethylpyridin-2(1H)-one monohydrochloride

[Formula 11]

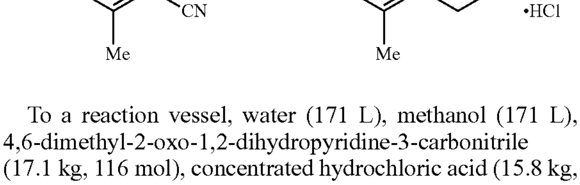

To a reaction vessel, water (171 L), methanol (171 L), 4,6-dimethyl-2-oxo-1,2-dihydropyridine-3-carbonitrile (17.1 kg, 116 mol), concentrated hydrochloric acid (15.8 kg, 152 mol) and 5% palladium carbon (55% moistened with water) (3.82 kg) were added, under a nitrogen atmosphere. Thereafter, the atmosphere in the reaction vessel was replaced with hydrogen gas. Then, the pressure of hydrogen gas was increased and the reaction mixture was stirred at 30° C. overnight. After completion of the reaction, the atmosphere in the reaction vessel was replaced with nitrogen gas. Palladium carbon was filtered off and washed with a 70% aqueous 2-propanol solution (51 L). To the filtrate, activated carbon (0.86 kg) was added and the resultant mixture was stirred for 30 minutes. Activated carbon was filtered off and washed with a 70% aqueous 2-propanol solution (51 L). The filtrate was concentrated to a volume of 103 L under reduced pressure, and then 2-propanol (171 L) was added to the concentrate. The resultant solution was concentrated again to a volume of 103 L under reduced pressure. Thereafter, 2-propanol (171 L) was added to the solution, which was stirred for one hour or more. After precipitation of a solid substance was confirmed, the mixture was concentrated to a volume of 103 L. Further, 2-propanol (51 L) was added to the concentrate, and then the mixture was concentrated again to a volume of 103 L under reduced pressure and stirred at 50° C. for 30 minutes. While keeping the internal temperature of the mixture at 40° C. or more, acetone (171 L) was added over one hour to the mixture. The mixture was stirred at 40 to 45° C. for 30 minutes, cooled to 25° C., and stirred for 2 hours or more. The solid substance precipitated was obtained by filtration, washed with acetone (86 L) and dried at 40° C. under reduced pressure to obtain the title compound (19.7 kg (yield 90.4%)). $^1$H NMR (500 MHz, methanol-$d_4$): δ 2.27 (s, 3H), 2.30 (s, 3H), 4.02 (s, 2H), 6.16 (s, 1H)

(Example 1-1) Production of methyl 5-chloro-3,4-dihydroxy-2-methylbenzoate

[Formula 12]

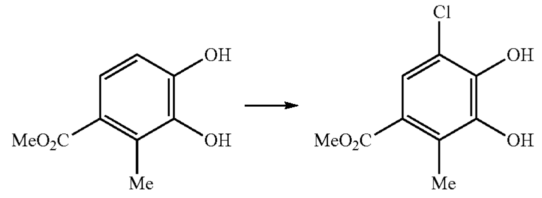

(1) (2)

To a reaction vessel, water (420 L), toluene (420 L), acetonitrile (420 L), and methyl 3,4-dihydroxy-2-methylbenzoate (1) (60 kg, 329 mol) were added, under a nitrogen atmosphere. After cooling, sulfuryl chloride (133.4 kg, 988 mol) was added dropwise to the reaction solution while keeping the temperature thereof at 20° C. or less. After completion of the reaction, the reaction solution was separated into organic layer 1 and a water layer. To the water layer, acetonitrile (60 L) and toluene (120 L) were added. After the mixture was stirred, the water layer was discarded to obtain organic layer 2. To organic layer 1, water (420 L) and acetonitrile (210 L) were added. After cooling, sulfuryl chloride (88.9 kg, 659 mol) was added dropwise to the mixture at 20° C. or less and further sulfuryl chloride (53.2 kg, 394 mol) was divided into portions, which were separately added. After completion of the reaction, the mixture was separated into organic layer 3 and a water layer. To the water layer, organic layer 2 was added. After the mixture was stirred, the water layer was discarded. The resultant organic layer was combined with organic layer 3. To the combined organic layer, water (420 L) and acetonitrile (210

L) were added. To this, sulfuryl chloride (44.5 kg, 329 mol) was added dropwise at 20° C. or less and further sulfuryl chloride (106.4 kg, 788 mol) was separated into portions and added. After completion of the reaction, the mixture was separated into organic layer 4 and a water layer. To the water layer, acetonitrile (60 L) and toluene (120 L) were added. After the mixture was stirred, the water layer was discarded and the organic layer was combined with organic layer 4. The combined organic layer was washed three times with a 20 wt % aqueous sodium chloride solution (300 L) and concentrated to 600 L under reduced pressure. To the concentrate, toluene (300 L) was added and the mixture was concentrated again to 600 L under reduced pressure. This operation was repeated twice, and then the mixture was heated with stirring at 60° C. for one hour. After the mixture was cooled to room temperature, the solid substance precipitated was obtained by filtration, washed with toluene (120 L), and dried at 40° C. under reduced pressure to obtain a crude product of the title compound (2) (52.1 kg (yield 73.0%)).

To a reaction vessel, toluene (782 L) and the crude product of the title compound (52.1 kg, 241 mol) were added, under a nitrogen atmosphere. The reaction mixture was warmed to 80° C. After confirming that crystals were completely dissolved, the mixture was filtered and washed with heated toluene (261 L). The filtrate was cooled to 60° C. for crystallization, followed by stirring for 0.5 hours. After the mixture was cooled to 10° C., the solid substance precipitated was obtained by filtration, washed with toluene (156 L) and dried at 40° C. under reduced pressure to obtain the title compound (2) (47.9 kg (yield 91.9%)).

$^1H$ NMR (500 MHz, methanol-$d_4$): δ 2.41 (s, 3H), 3.82 (s, 3H), 7.41 (s, 1H)

(Example 1-2) Study 1 of Chlorination Conditions

Since it is difficult, even in later steps, to remove compound (1), which is a raw material, and compound (4), which is a reaction by-product, it is necessary to control the amount of the compound (1) remaining unreacted and the amount of the compound (4) to be produced. Therefore, chlorination was carried out in the same manner as in Example 1-1 using compound (1) as a raw material. The results are shown in Table 1.

[Formula 13]

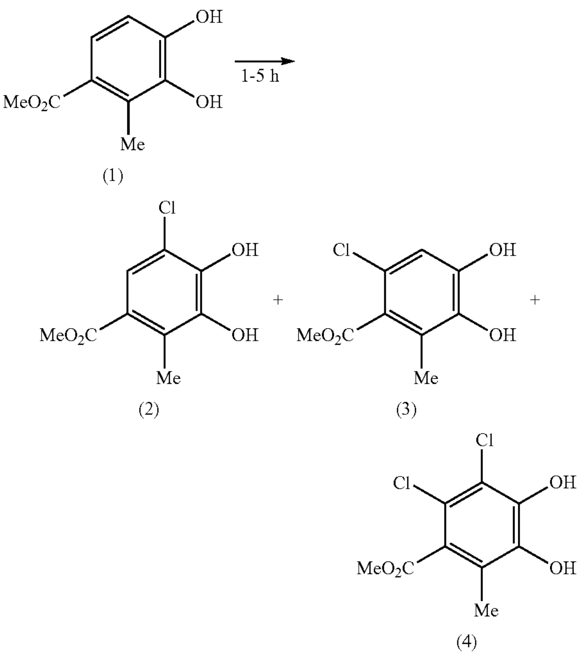

(1) (2) + (3) + (4)

TABLE 1

| No | Reagent (eq.) | Solvent (vol) | Temp. | HPLC(220 nm, area %) Comp.2 | Comp.3 | Comp.4 | Comp.1 |
|---|---|---|---|---|---|---|---|
| 1 | NCS(2.0) Anisole(1.0) | EtOAc(10) | rt | 55.3 | 3.3 | 7.6 | 11.3 |
| 2 | NCS(1.5) Anisole (1.0) | $CH_3CN$(10) | rt | 28.6 | 5.2 | 1.3 | 59.6 |
| 3 | $SO_2Cl_2$(1.5) | $CH_3CN$(20) | 0° C. | 64.5 | 8.8 | 14.3 | 9.9 |
| 4 | DCH(0.5) | $CH_3CN$(10) | rt | 43.1 | 13.6 | 18.7 | 19.8 |
| 5 | Na—diCl(0.5) | $CH_3CN$(10) | rt | 28.2 | 1.4 | 7.8 | 24.9 |
| 6 | TriCl(0.33) | $CH_3CN$(10) | rt | 40.0 | 12.5 | 24.3 | 17.0 |
| 7 | $SO_2Cl_2$(1.0) MeOH(1.0) | toluene(10) | rt | 23.0 | 8.3 | 17.4 | 49.6 |
| 8 | $SO_2Cl_2$(1.0) i-$Bu_2NH$(0.05) | toluene(10) | rt | 9.1 | 16.3 | 29.0 | 42.1 |
| 9 | NaClOaq(2.5) 2M HCl(3.0) | CPME(10) | rt | 68.6[a] | ND | ND | 0.4 |
| 10 | 30% $H_2O_2$(1.0) 2M HCl/EtOAc (2.0) | DMF(10) | 50° C. | 34.5 | 24.3 | 6.6 | 32.8 |
| 11 | 30% $H_2O_2$(1.1) c-HCl(2.0) | MeOH(10) | reflux | 23.7 | 8.1 | 0.8 | 63.2 |

NCS: N-chlorosuccinimide,

DCH: 1,3-dichloro-5,5-dimethylhydantoin,

Na—diCl: sodium dichloroisocyanurate,

TriCl: trichloroisocyanuric acid

[a]quantified by HPLC: 33.5%

HPLC Conditions

Detection: 220 nm

Column: ACQUITY UPLC BEH C18 (2.1 mm ID×50 mm, 1.7 μm, Waters)

Column temperature: 40° C.

Mobile phase: A: 0.1 vol % aqueous trifluoroacetic acid solution, B: acetonitrile Gradient Condition:

TABLE 2

| | Time (min) | | | | |
|---|---|---|---|---|---|
| | 0 | 3 | 4 | 4.01 | 5 |
| Concentration of solution B | 10 | 70 | 90 | 10 | 10 |

Flow rate: 1.0 mL/min

Injection amount: 1 μL

Solution for dissolving sample: acetonitrile/water (1:1)

Wash solution: acetonitrile/water (1:1)

Purge solution: acetonitrile/water (1:1)

Seal wash solution: acetonitrile/water (1:1)

Sample-cooler temperature: not specified

Measurement time: 5 minutes

Time for measuring area: about 0.5 minutes-4.0 minutes

Comp. 1: 1.11 min, Comp. 2: 1.55 min,

Comp. 3: 1.44 min, Comp. 4: 1.70 min (Example 1-3) Study 2 of Chlorination Conditions Using the compound (1) as a starting material and sulfuryl chloride as a chlorination reagent, chlorination in various solvents was examined. The results are shown in Table 3.

TABLE 3

| | Solvent | $SO_2Cl_2$ | | HPLC(220 nm, area %) | | | |
|---|---|---|---|---|---|---|---|
| No. | (vol) | (eq.) | Temp | Comp.2 | Comp.3 | Comp.4 | Comp.1 |
| 1 | $CH_3CN$(20) | 1.5 | 0° C. | 64.5 | 8.8 | 14.3 | 9.9 |
| 2 | EtOAc(20) | 1.5 | −20° C. | 69.0 | 6.7 | 8.7 | 10.8 |
| 3 | THF(20) | 1.9 | −20° C. | 72.8 | 4.0 | 18.0 | 2.3 |
| 4 | CPME(20) | 5.0 | −20° C. | 64.1 | 4.3 | 4.4 | 14.4 |
| 5 | DMAc | 1.0 | −20° C. | 32.4 | 6.3 | 4.3 | 50.0 |
| 6 | $CH_3CN—H_2O$ 1/1(20) | 5.0 | 0° C. | 28.8 | 0.4 | 0.4 | 66.0 |
| 7 | CPME-$H_2O$ 1/1(20) | 3.0 | 0° C. | 45.6 | 8.7 | 2.3 | 39.0 |
| 8 | CPME-$CH_3CN—H_2O$ 1/1/1(15) | 1.0 | 0° C. | 28.0 | 2.2 | 0.6 | 65.7 |
| 9 | MTBE-$CH_3CN—H_2O$ 1/1/1(15) | 1.0 | 0° C. | 23.4 | 3.4 | 3.4 | 66.5 |
| 10 | Toluene-$CH_3CN—H_2O$ 1/1/1(30) | 6.0 | 0° C. | 83.6 | 3.4 | 4.1 | 5.0 |
| 11 [a] | Toluene-$CH_3CN—H_2O$ 1/1/1(21) | 9.6 | <20° C. | 89.6 | 1.1 | 1.9 | 2.5 |

[a] Isolation yield: 73.0%

* When toluene alone was used as a solvent, a reaction did not virtually proceed.

(Example 2) Production of methyl (2RS)-2-{trans-4-[(tert-butoxycarbonyl)amino]cyclohexyl}-7-chloro-2,4-dimethyl-1,3-benzodioxole-5-carboxylate

[Formula 14]

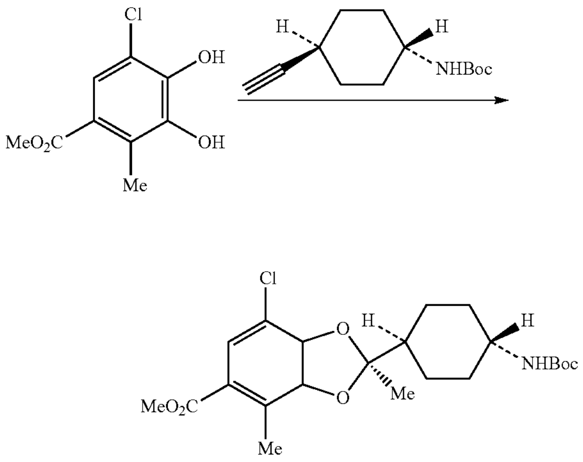

To a reaction vessel, toluene (9.0 L), tert-butyl (trans-4-ethynylcyclohexyl)carbamate (2.23 kg, 9.99 mol), methyl 5-chloro-3,4-dihydroxy-2-methylbenzoate (1.80 kg, 8.31 mol), tri(o-tolyl)phosphine (76.0 g, 250 mmol) and triruthenium dodecacarbonyl (53.0 g, 82.9 mmol) were added, under a nitrogen atmosphere. The reaction solution was heated with stirring at 80-90° C. for 7 hours while supplying an oxygen-containing nitrogen gas. The reaction solution was cooled to room temperature to obtain a toluene solution of the title compound.

(Example 3) Production of (2RS)-2-{trans-4-[(tert-butoxycarbonyl)amino]cyclohexyl}-7-chloro-2,4-dimethyl-1,3-benzodioxole-5-carboxylic acid

[Formula 15]

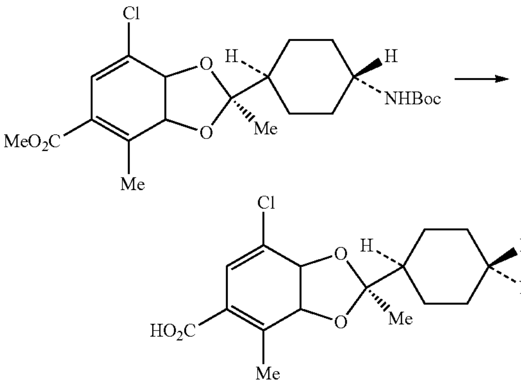

To the toluene solution (13 L, 7.83 mol equivalent) of methyl (2RS)-2-{trans-4-[(tert-butoxycarbonyl)amino]cyclohexyl}-7-chloro-2,4-dimethyl-1,3-benzodioxole-5-carboxylate obtained in Example 2, methanol (9.0 L), 1,2-dimethoxyethane (3.6 L) and a 5 mol/L aqueous sodium hydroxide solution (2.50 L, 12.5 mol) were added. The reaction solution was stirred at 55-65° C. for 3 hours. After water (5.4 L) was added, the reaction solution was separated into an organic layer and a water layer. After the water layer was cooled to room temperature, 1,2-dimethoxyethane (16.2 L) was added to the water layer and the pH thereof was adjusted to 4.0 to 4.5 with 3 mol/L hydrochloric acid, and then toluene (5.4 L) was added. After heating to 50-60° C., the mixture was separated into an organic layer and a water layer. The organic layer was washed with a 20 wt % aqueous sodium chloride solution (7.2 L). Then, to the organic layer, 1,2-dimethoxyethane (21.6 L) was added. The mixture was concentrated to 9 L under reduced pressure, and thereafter, 1,2-dimethoxyethane (21.6 L) was added to the mixture. Thereafter, the mixture was heated up to 50-60° C. and filtered to remove inorganic substances. Subsequently, the filtrate was washed with 1,2-dimethoxyethane (1.8 L) and concentrated to 21.6 L under reduced pressure to obtain a 1,2-dimethoxyethane solution (quantitative value 89.6% (total yield from Example 2 to 3), 7.45 mol equivalent) of the title compound.

(Example 4) Production of (1S)-1-phenylethanaminium (2R)-2-{trans-4-[(tert-butoxycarbonyl)amino]cyclohexyl}-7-chloro-2,4-dimethyl-1,3-benzodioxole-5-carboxylate

[Formula 16]

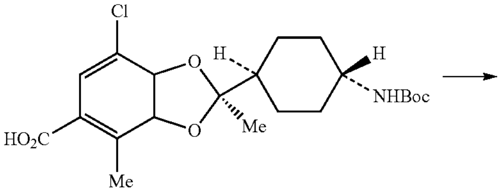

-continued

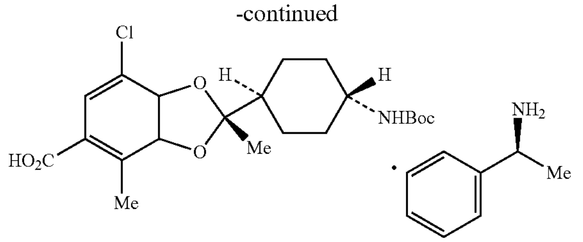

The dimethoxyethane solution (21.6 L, 7.45 mol equivalent) of (2R5)-2-{trans-4-[(tert-butoxycarbonyl)amino]cyclohexyl}-7-chloro-2,4-dimethyl-1,3-benzodioxole-5-carboxylic acid obtained in Example 3 was warmed up to 75-80° C. Thereafter, (1S)-1-phenylethanamine (1.02 kg, 8.42 mmol) was added to the solution and the mixture was stirred for 4 hours. A mixture of 1,2-dimethoxyethane (9.2 L) and water (3.4 L) heated to 50-60° C. was added to the resultant solution. After stirring, the mixture was cooled to room temperature. The solid substance precipitated was obtained by filtration and washed with 1,2-dimethoxyethane (9 L) to obtain a crude product of the title compound (1.75 kg (on a dry basis), yield 38.5% (total yield from Example 2), optical purity 93.8% ee).

To a reaction vessel, an aqueous 1,2-dimethoxyethane solution (13.6 L) and the crude product (amount equivalent to 1.70 kg, 3.11 mol) of (1S)-1-phenylethanaminium (2R)-2-{trans-4-[(tert-butoxycarbonyl)amino]cyclohexyl}-7-chloro-2,4-dimethyl-1,3-benzodioxole-5-carboxylate obtained in Step 1 were added, under a nitrogen atmosphere, and then 5 mol/L hydrochloric acid (0.56 L, 2.8 mol) was added dropwise. After the reaction solution was stirred at room temperature for 10 minutes or more and heated up to 75° C. or more, a solution, which was prepared by dissolving (1S)-1-phenylethanamine (360 g, 2.97 mmol) in 1,2-dimethoxyethane (2.6 L), was added dropwise over one hour or more to the reaction solution. Thereafter, the reaction mixture was washed with 1,2-dimethoxyethane (0.9 L), stirred for 2 hours, and cooled to 0-5° C. The solid substance precipitated was obtained by filtration, washed with 1,2-dimethoxyethane (5.1 L) cooled to 0-5° C., to obtain the title compound (1.56 kg on a dry basis, yield 91.9%, optical purity 99.5% ee).

$^1$HNMR (500 MHz, methanol-$d_4$): δ 1.15-1.23 (m, 2H), 1.28-1.35 (m, 2H), 1.42 (s, 9H), 1.59 (s, 3H), 1.60-1.61 (d, 3H, J=7.0 Hz, 3H), 1.80-1.86 (dt, J=12.0, 3.0 Hz, 1H), 1.95-1.96 (m, 4H), 2.27 (s, 3H), 3.24-3.28 (m, 1H), 4.39-4.43 (q, J=7.0 Hz, 1H), 7.07 (s, 1H), 7.37-7.45 (m, 5H)

(Example 5) Production A of (2R)-7-chloro-2-[trans-4-(dimethylamino)cyclohexyl]-2,4-dimethyl-1,3-benzodioxole-5-carboxylic acid monohydrochloride

[Formula 17]

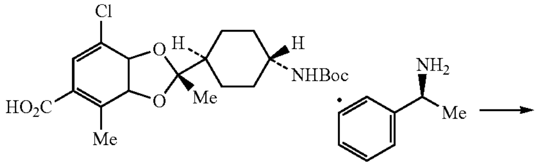

-continued

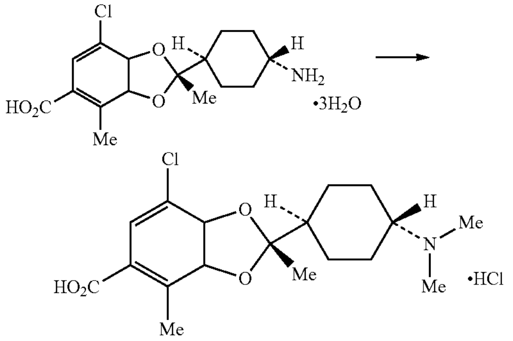

(Step 1)

To a reaction vessel, 1,2-dimethoxyethane (200 L), (1S)-1-phenylethanaminium (2R)-2-{trans-4-[(tert-butoxycarbonyl)amino]cyclohexyl}-7-chloro-2,4-dimethyl-1,3-benzodioxole-5-carboxylate (amount equivalent to 87.64 kg, 160 mol) and 35% hydrochloric acid (16.7 kg, 160 mol) were added, under a nitrogen atmosphere. The reaction solution was heated to 45-55° C. and 35% hydrochloric acid (36.7 kg, 352 mol) was divided into 7 portions, which were separately added dropwise thereto, stirred for 3 hours, cooled to room temperature, and added to a mixture of water (982 L) and a 5 mol/L sodium hydroxide solution (166.34 kg, 702 mol). To the resultant solution, 3 mol/L hydrochloric acid (22.4 kg) was added dropwise at 30° C. After confirming precipitation of crystals, the mixture was stirred for 30 minutes or more, cooled to 10° C., and further stirred for 2 hours. Thereafter, 3 mol/L hydrochloric acid (95.1 kg) was further added dropwise to the mixture at 10° C. to adjust the pH to 7.0. The solid substance precipitated was obtained by filtration, washed with water (293 L) cooled to 10° C. to obtain (2R)-2-(trans-4-aminocyclohexyl)-7-chloro-2,4-dimethyl-1,3-benzodioxole-5-carboxylic acid trihydrate (57.63 kg (on a dry basis), yield 94.7%).

$^1$H NMR (500 MHz, methanol-$d_4$+$D_2O$): 1.32-1.44 (m, 4H), 1.61 (s, 3H), 1.89-1.94 (m, 1H), 2.01-2.13 (m, 4H), 2.27 (s, 3H), 2.99-3.07 (m, 1H), 7.06 (s, 3H)

(Step 2)

To a reaction vessel, 1,2-dimethoxyethane (115 L), (2R)-2-(trans-4-aminocyclohexyl)-7-chloro-2,4-dimethyl-1,3-benzodioxole-5-carboxylic acid trihydrate (amount equivalent to 57.63 kg, 152 mmol), formic acid (34.92 kg, 759 mol) and a 37% aqueous formaldehyde solution (93.59 kg, 1153 mol) were added, under a nitrogen atmosphere. The reaction solution was stirred at 55-65° C. for 2 hours and cooled to room temperature. To the reaction solution, 2-propanol (864 L) was added. The solution was concentrated to 576 L under reduced pressure. To the solution, 2-propanol (231 L) was added and the solution was again concentrated to 576 L under reduced pressure. Further, 2-propanol (231 L) was added to the solution and the solution was concentrated to 576 L under reduced pressure. Thereafter, 35% hydrochloric acid (20.40 kg, 196 mol) was added dropwise to the solution over 2 hours. The mixture was stirred at room temperature for 30 minutes. To the resulting slurry, ethyl acetate (576 L) was added over 30 minutes. The mixture was concentrated to 692 L. After ethyl acetate (461 L) was added to the mixture, the mixture was further concentrated to 519 L. To the residue, ethyl acetate (634 L) was added and the resultant residue was stirred at room temperature for 2 hours. The solid substance precipitated was obtained by filtration, washed with ethyl acetate (491 L) and dried at 40° C. under reduced pressure to obtain the title compound (51.56 kg, yield 87.1%).

$^1$H NMR (500 MHz, methanol-$d_4$): δ 1.38-1.47 (m, 2H), 1.53-1.61 (m, 2H), 1.67 (s, 3H), 1.99-2.05 (m, 1H), 2.13-2.18 (m, 4H), 2.38 (s, 3H), 2.84 (s, 6H), 3.19-3.25 (dt, J=12.5, 3.5 Hz, 1H), 7.53 (s, 1H)

(Example 6) Production B of (2R)-7-chloro-2-[trans-4-(dimethylamino)cyclohexyl]-2,4-dimethyl-1,3-benzodioxole-5-carboxylic acid monohydrochloride

[Formula 18]

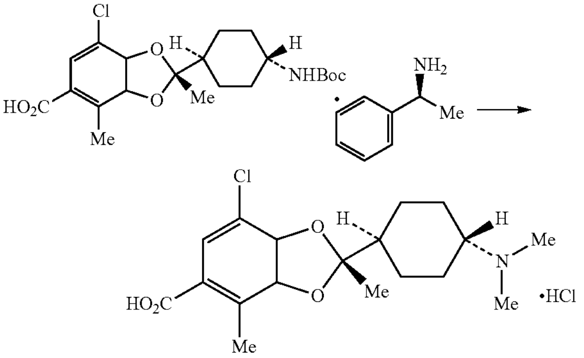

To a reaction vessel, formic acid (20 mL), a 37% aqueous formaldehyde solution (15 mL), dimethoxyethane (10 mL) and (1S)-1-phenylethanaminium (2R)-2-{trans-4-[(tert-butoxycarbonyl)amino]cyclohexyl}-7-chloro-2,4-dimethyl-1,3-benzodioxole-5-carboxylate (10 g, 18.3 mmol) were added, under a nitrogen atmosphere. The reaction solution was stirred at 80° C. for 10 hours and cooled to room temperature. After insoluble matter was filtered off, 2-propanol (100 mL) was added to the filtrate, which was subsequently concentrated to a volume of 30 mL under reduced pressure. While stirring the filtrate at room temperature, ethyl acetate (120 mL) and concentrated hydrochloric acid (6.1 mL) were added to the filtrate to obtain a slurry. The slurry was concentrated to 30 mL under reduced pressure, and ethyl acetate (120 mL) was added thereto, and then the slurry was concentrated again to 30 mL under reduced pressure. After ethyl acetate (120 mL) was added, the solid substance precipitated was obtained by filtration, washed with ethyl acetate (50 mL) and dried at 40° C. under reduced pressure to obtain the title compound (6.56 g (yield 92.0%)).

(Example 7) Production of (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluenesulfonate

[Formula 19]

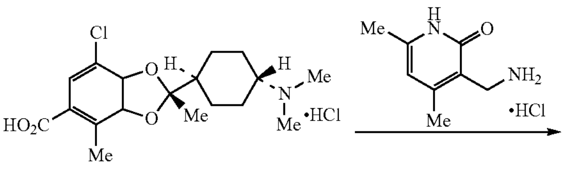

-continued

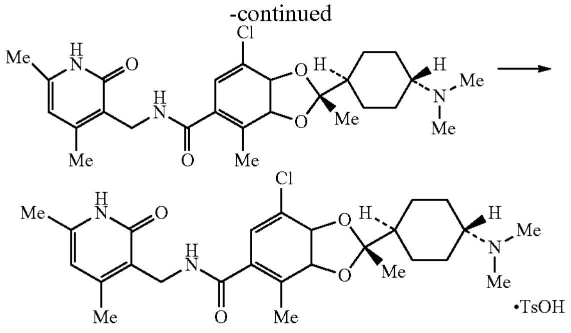

To a reaction vessel, acetone (6.5 L), purified water (1.3 L), (2R)-7-chloro-2-[trans-4-(dimethylamino)cyclohexyl]-2,4-dimethyl-1,3-benzodioxole-5-carboxylic acid monohydrochloride (650.4 g, 1.67 mol), 3-(aminomethyl)-4,6-dimethylpyridin-2(1H)-one monohydrochloride (330.1 g, 1.75 mol) and triethylamine (337 g, 3.33 mol) were added under a nitrogen atmosphere. The reaction mixture was stirred at room temperature for 30 minutes. Thereafter, 1-hydroxybenzotriazole monohydrate (255 g, 1.67 mol) and 1-ethyl-3-(dimethylaminopropyl) carbodiimide hydrochloride (383 g, 2.00 mmol) were added to the reaction mixture. The reaction mixture was stirred at room temperature overnight. After the pH of the reaction solution was adjusted to 11 with a 5 mol/L sodium hydroxide solution, toluene (9.8 L) was added thereto. The reaction solution was stirred, and then separated into organic layer 1 and a water layer. To the water layer, toluene (3.3 L) was added. The mixture was stirred and a water layer was discarded. The organic layer thus obtained was combined with organic layer 1 previously obtained. The combined organic layer was concentrated to 9.75 L under reduced pressure and toluene (6.5 L) was added thereto. The resultant mixture was washed twice with purified water (3.25 L). The organic layer obtained was concentrated to 4.875 L under reduced pressure and 2-propanol (1.625 L) was added thereto. A solution was prepared by dissolving p-toluenesulfonic acid monohydrate (0.12 kg, 0.631 mol) in 4-methyl-2-pentanone (1.14 L) and added dropwise to the organic layer heated to 68° C. over 1.5 hours. The mixture was stirred at 68° C. for 30 minutes. Further, a solution, which was prepared by dissolving p-toluenesulfonic acid monohydrate (0.215 kg, 1.13 mol) in 4-methyl-2-pentanone (2.11 L), was added dropwise over 3.5 hours. The resultant mixture was stirred at 68° C. for 30 minutes. Thereafter, 4-methyl-2 pentanone (6.5 L) was added dropwise over one hour. The mixture was cooled to room temperature and the solid substance precipitated was obtained by filtration, washed with 4-methyl-2-pentanone (3.25 L) and dried at 40° C. under reduced pressure to obtain a crude product of the title compound (1.035 kg (yield 94.2%)).

To a reaction vessel, 2-propanol (6.65 L) and the crude product (950 g) of the title compound obtained above were added under a nitrogen atmosphere. The mixture was stirred and purified water (0.23 L) was added thereto. After a solid substance was completely dissolved in the solution at 68° C., the solution was filtered and washed with hot 2-propanol (0.95 L). After confirming that a solid substance was completely dissolved at an internal temperature of 68° C., the solution was cooled to 50° C. Thereafter, a seed crystal* (9.5 g, 0.01 wt) was added and the resultant slurry was stirred at 50° C. overnight. To the mixture, tert-butyl methyl ether (11.4 L) was separated into 4 portions, which were separately added dropwise each over 30 minutes. Every time a portion was added, the mixture was stirred for 30 minutes. After the resultant mixture was cooled to room temperature, the solid substance precipitated was obtained by filtration, washed with a mixture of 2-propanol (0.38 L) and tert-butyl methyl ether (3.42 L), followed with tert-butyl methyl ether (4.75 L), and dried at 40° C. under reduced pressure to obtain the title compound (915.6 g, yield 96.4%).

*Process for forming seed crystal $^1$HNMR (500 MHz, methanol-$d_4$): δ 1.35-1.43 (m, 2H), 1.49-1.57 (m, 2H), 1.62 (s, 3H), 1.94-2.00 (dt, J=12.5, 3.0 Hz, 1H), 2.09-2.13 (m, 4H), 2.17 (s, 3H), 2.24 (s, 3H), 2.35 (s, 3H), 2.36 (s, 3H), 2.82 (s, 6H), 3.16-3.22 (dt, J=12.0, 3.5 Hz, 1H), 4.42 (s, 2H), 6.10 (s, 1H), 6.89 (s, 1H), 7.22-7.24 (d, J=8.0 Hz, 2H), 7.69-7.71 (dt, J=8.0, 1.5 Hz, 2H)

To a reaction vessel, 2-propanol (79.0 L) and the crude product of the title compound (7.90 kg) were added under a nitrogen atmosphere. The reaction mixture was stirred and purified water (7.9 L) was added thereto to completely dissolve a solid substance. Further, activated carbon (0.40 kg) was added, stirred, filtered and washed with 2-propanol (79.0 L). The filtrate was concentrated to 58 L. To the residue, 2-propanol (5 L) was added and the mixture was warmed up to 64° C. To the mixture, tert-butyl methyl ether (19.8 L) was added. After confirming precipitation of crystals, further tert-butyl methyl ether (75.1 L) was divided into three portions, which were separately added. Every time a portion was added, the mixture was stirred for 30 minutes. After the resultant mixture was cooled to room temperature, the solid substance precipitated was obtained by filtration, washed with a mixture of 2-propanol (7.9 L) and tert-butyl methyl ether (15.8 L), and dried at 40° C. under reduced pressure to obtain the title compound (7.08 kg, yield 89.6%) serving as a seed crystal.

The crystals of (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluenesulfonate obtained in Example 7 were analyzed by powder X-ray diffraction. Diffraction angle (2θ), lattice spacing (d value) and relative intensity in a powder X-ray diffraction spectrum are listed in Table 4.

TABLE 4

| | 2θ(°) | d-value(Å) | Relative intensity(%) |
|---|---|---|---|
| 1 | 13.86 | 6.3841 | 66 |
| 2 | 15.06 | 5.8780 | 58 |
| 3 | 15.24 | 5.8090 | 65 |
| 4 | 17.62 | 5.0293 | 52 |
| 5 | 18.80 | 4.7162 | 83 |
| 6 | 19.08 | 4.6476 | 95 |
| 7 | 20.16 | 4.4010 | 82 |
| 8 | 21.66 | 4.0995 | 100 |
| 9 | 23.30 | 3.8145 | 99 |
| 10 | 25.58 | 3.4795 | 76 |

The invention claimed is:

1. A production method comprising reacting a compound represented by formula (II):

(II)

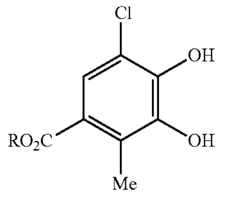

with tert-butyl (trans-4-ethynylcyclohexyl) carbamate using a ruthenium catalyst to obtain a compound represented by formula (III):

(III)

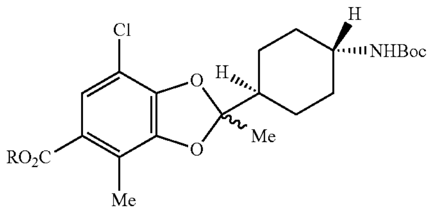

wherein R represents a $C_1$-$C_6$ alkyl group; and wherein the ruthenium catalyst is a catalyst comprising $Ru_{13}(CO)_{12}$ and $P(o\text{-}Tol)_3$.

2. The production method according to claim 1, wherein R is a methyl group.

3. The production method according to claim 1, further comprising subjecting the compound represented by formula (III) to:

(i) a step of performing hydrolysis;

(ii) a step of performing optical resolution using an optically active amine;

(iii) a step of removing the Boc group; and (iv) a step of performing dimethylation of the nitrogen atom, to obtain a compound represented by formula (IV):

(IV)

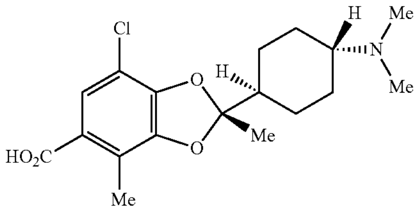

or a pharmaceutically acceptable salt thereof.

4. The production method according to claim 3, wherein the optically active amine is (1S)-1-phenylethanamine.

5. The production method according to claim 3, further comprising condensing the compound represented by formula (IV) with 3-(aminomethyl)-4,6-dimethylpyridin-2(1H)-one or a salt thereof to obtain a compound represented by formula (V):

(V)

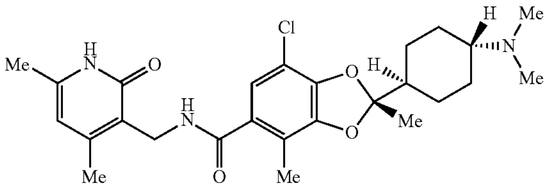

or a pharmaceutically acceptable salt thereof.

6. The production method according to claim 1, further comprising obtaining the compound represented by formula (II) by chlorinating a compound represented by formula (I):

(I)

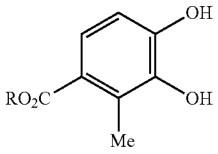

with sulfuryl chloride in a solvent.

7. The production method according to claim 6, wherein the solvent is a solvent comprising at least one selected from toluene, acetonitrile, methyl tert-butyl ether and cyclopentyl methyl ether, and water.

8. The production method according to claim 6, wherein the solvent is a solvent comprising toluene, acetonitrile and water.

9. The production method according to claim 6, wherein the solvent is at least one solvent selected from acetonitrile, ethyl acetate, tetrahydrofuran, dimethylacetamide and cyclopentyl methyl ether.

10. The production method according to claim 6, wherein R is a methyl group.

11. The production method according to claim 6, further comprising subjecting the compound represented by formula (III) to:

(i) a step of performing hydrolysis;

(ii) a step of performing optical resolution using an optically active amine;

(iii) a step of removing the Boc group; and (iv) a step of performing dimethylation of the nitrogen atom, to obtain a compound represented by formula (IV):

(IV)

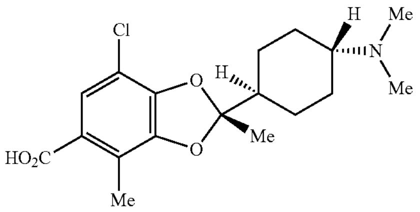

or a pharmaceutically acceptable salt thereof.

12. The production method according to claim 11, wherein the optically active amine is (1S)-1-phenylethanamine.

13. The production method according to claim 6, further comprising condensing the compound represented by formula (IV) with 3-(aminomethyl)-4,6-dimethylpyridin-2(1H)-one or a salt thereof to obtain a compound represented by formula (V):

(V)

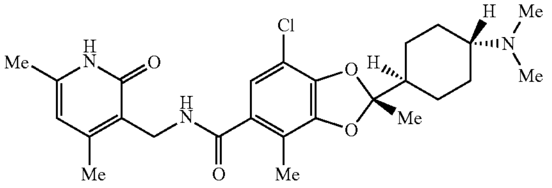

or a pharmaceutically acceptable salt thereof.

14. The production method according to claim 11, further comprising condensing the compound represented by formula (IV) with 3-(aminomethyl)-4,6-dimethylpyridin-2(1H)-one or a salt thereof to obtain a compound represented by formula (V):
(V)
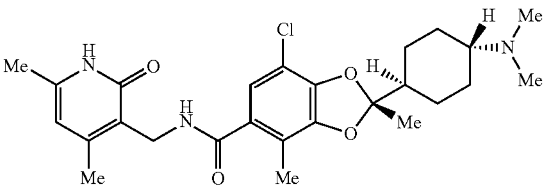
or a pharmaceutically acceptable salt thereof.
* * * * *